(12) United States Patent
Tritsch et al.

(10) Patent No.: US 7,632,518 B2
(45) Date of Patent: Dec. 15, 2009

(54) 25-HYDROXY VITAMIN $D_3$ COMPOSITIONS

(75) Inventors: Jean-Claude Tritsch, Montville, NJ (US); Li-Qun Yu, Naperville, IL (US); Stephen Thomas Mazzaro, Staten Island, NY (US)

(73) Assignee: DSM IP Assets B.V., TE Heerlen (NL)

( * ) Notice: Subject to any disclaimer, the term of this patent is extended or adjusted under 35 U.S.C. 154(b) by 321 days.

(21) Appl. No.: 10/341,099

(22) Filed: Jan. 13, 2003

(65) Prior Publication Data

US 2003/0170324 A1   Sep. 11, 2003

Related U.S. Application Data

(60) Provisional application No. 60/350,301, filed on Jan. 15, 2002.

(51) Int. Cl.
| | |
|---|---|
| *A23K 1/165* | (2006.01) |
| *A23K 1/17* | (2006.01) |
| *A61K 47/00* | (2006.01) |
| *A61K 36/889* | (2006.01) |
| *A61K 31/655* | (2006.01) |
| *A61K 31/355* | (2006.01) |
| *A01N 43/16* | (2006.01) |
| *A01N 51/00* | (2006.01) |

(52) U.S. Cl. ............... 424/442; 514/157; 514/458; 424/727; 424/439

(58) Field of Classification Search ........... 424/442, 424/727, 439; 514/157, 458
See application file for complete search history.

(56) References Cited

U.S. PATENT DOCUMENTS

| | | | |
|---|---|---|---|
| 3,565,924 A | | 2/1971 | De Luca et al. |
| 4,310,467 A | | 1/1982 | Batcho et al. |
| 5,043,170 A | * | 8/1991 | Borenstein et al. ............ 426/73 |
| 5,316,770 A | * | 5/1994 | Edwards, Jr. ............... 424/442 |
| 5,476,661 A | | 12/1995 | Pillai et al. |
| 5,695,794 A | * | 12/1997 | Stark et al. ..................... 426/2 |
| 6,011,016 A | * | 1/2000 | Schmidt et al. ............... 514/23 |
| 6,248,374 B1 | | 6/2001 | Murray et al. |
| 2007/0082089 A1 | | 4/2007 | Krammer et al. |

FOREIGN PATENT DOCUMENTS

EP   0 711 558 A1   5/1996

OTHER PUBLICATIONS

Stedman's Medical Dictionary (27th edition) Vitamin D.*
Smith et al. (The J of Clin Investigation, 50, 1971, 2159-2167).*
Rovimix Document (2009)—Dr. Tritsch's presentation—Sep. 17, 2009.*
Farquharson et al, "Chondrocytes and Longitudinal Bone Growth: The Development of Tibial Dyschondroplasia", 2000 Poultry Science 78:994-1004.

* cited by examiner

*Primary Examiner*—Sreeni Padmanabhan
*Assistant Examiner*—Umamaheswari Ramachandran
(74) *Attorney, Agent, or Firm*—Nixon & Vanderhye P.C.

(57) ABSTRACT

An oil composition containing 25-hydroxy Vitamin $D_3$ and an oil is provided. In addition an emulsion, a microencapsulated oil composition, and a feed premix composition each containing 25-hydroxy Vitamin $D_3$ are provided. Methods of making an oil composition, a microencapsulated oil composition, and a feed premix containing 25-hydroxy Vitamin $D_3$ are also provided.

29 Claims, 8 Drawing Sheets

Figure 1. Stability at 11°C - % active ingredient by weight.

Figure 2. Stability at 11°C - % retention of the active ingredient.

Figure 3. Stability at 25°C - % active ingredient by weight.

Figure 4. Stability at 25°C - % retention of the active ingredient.

Figure 5. Linear regression of percent retention of 25-hydroxy Vitamin $D_3$.

Figure 6. Stability of Vitamin $D_3$ and 25-hydroxy Vitamin $D_3$ formulations in the basic premix.

Figure 7. Stability of Vitamin $D_3$ and 25-hydroxy Vitamin $D_3$ formulations in the vitamin premix.

Figure 8. Stability of Vitamin $D_3$ and 25-hydroxy Vitamin $D_3$ formulations in the complete premix.

25-HYDROXY VITAMIN D₃ COMPOSITIONS

This application claims benefit under 35 U.S.C. §119(e) of U.S. Provisional Application No. 60/350,301, filed Jan. 15, 2002.

FIELD OF THE INVENTION

The present invention relates to compositions containing 25-hydroxy Vitamin D$_3$, including oils, emulsions, microencapsulated oils, and feed premixes. The invention also relates to methods of making and using such compositions.

BACKGROUND OF THE INVENTION

Vitamins are useful as nutritional supplements in the diet of various animals. Vitamins act as catalysts in nearly every biochemical pathway. For that reason vitamin deficiency leads to numerous diseases and physical ailments.

Vitamin D$_3$ is implicated in numerous diseases. Too much or too little Vitamin D$_3$ in the parathyroid can lead to hyperparathyroidism, hypoparathyroidism, pseudohypoparathyroidism, and secondary hyperparathyroidism. In the pancreas Vitamin D$_3$ is implicated in diabetes. In the liver, problems with Vitamin D$_3$ can lead to cirrhosis, and obstructive jaundice. Vitamin D$_3$ is intimately involved in the regulation of calcium levels and in the bone is implicated in fibrogenisis imperfecta ossium, osteitis fibrosa cystica, osteomalacia, osteoporosis, osteopenia, osteosclerosis, renal osteodystrophy, and rickets. In the intestine, Vitamin D$_3$ plays a role in glucocorticoid antagonism, idiopathic hypercalcemia, malabsorption syndrome, and tropical sprue. Psoriasis in the skin, medullary carcinoma in the thyroid, sarcoidosis in the lung, and hypophosphatemic VDRR and chronic renal disease in the kidney are all affected by the levels of Vitamin D$_3$ in the body.

Vitamin D$_3$ is produced by the skin under normal sunlight conditions through the oxidation of cholesterol. Vitamin D$_3$ is then converted by the liver into 25-hydroxy Vitamin D$_3$. Finally, 25-hydroxy Vitamin D$_3$ is converted by the kidney into 1α,25(OH)$_2$ Vitamin D$_3$, which is active in various biochemical pathways.

The production of 1α,25(OH)$_2$ Vitamin D$_3$ is shown below.

25-hydroxy Vitamin $D_3$ is a reservoir of the downstream $1\alpha,25$-hydroxy Vitamin $D_3$ in the body. When the level of Vitamin $D_3$ is adequate, 25-hydroxy Vitamin $D_3$ is stored in the liver. It is released from the liver, as required, and further processed by the kidney into the active molecule.

For these reasons, it is useful to provide 25-hydroxy Vitamin $D_3$ to animals as a nutritional supplement. Formulations containing 25-hydroxy Vitamin $D_3$ are sold under the trademark HY-D (Roche Vitamins Inc., Parsippany, N.J.).

Unfortunately, 25-hydroxy Vitamin $D_3$ is unstable under conventional storage conditions, resulting in a time-dependent loss of activity per unit mass. Among other things, 25-hydroxy Vitamin $D_3$ is prone to oxidation, particularly during storage over extended periods of time. Such degradation can adversely affect dosing of 25-hydroxy Vitamin $D_3$ when incorporated into animal feeds.

It would, therefore, be advantageous to provide 25-hydroxy Vitamin $D_3$ compositions with improved stability characteristics under a wide spectrum of conditions and in combination with various nutritional additives. These and other objects of the present invention are described in greater detail below.

SUMMARY OF THE INVENTION

The present invention provides an oil composition containing an oil and 25-hydroxy Vitamin $D_3$, wherein the 25-hydroxy Vitamin $D_3$ is dissolved in the oil in an amount between about 5% and 50% by weight based on the total weight of the oil composition.

The present invention also provides an emulsion comprising an aqueous composition and an oil composition, wherein the oil composition comprises 25-hydroxy Vitamin $D_3$ dissolved in the oil in an amount between about 5% and about 50% by weight based on the total weight of the oil composition.

Also provided is a microencapsulated oil comprising an oil composition and an encapsulation agent encapsulating the oil composition, wherein the oil composition contains 25-hydroxy Vitamin $D_3$ dissolved in an amount between about 5% and 50% by weight based on the total weight of the oil composition. In addition, a method of making the microencapsulated oil is provided, comprising providing an oil composition wherein 25-hydroxy Vitamin $D_3$ is dissolved in an oil in an amount between about 5% and 50% by weight based on the total weight of the oil composition, and encapsulating the oil composition in encapsulating agent.

The present invention also provides a feed premix composition comprising a microencapsulated oil of the invention admixed with at least one nutritional additive. Also provided is a method of making the feed premix composition, comprising providing a microencapsulated oil comprising an oil composition, wherein 25-hydroxy Vitamin $D_3$ is dissolved in an oil in an amount between about 5% and about 50% by weight based on the total weight of the oil composition encapsulated in an encapsulating agent. The microencapsulated oil composition is then admixed with a nutritional additive.

DETAILED DESCRIPTION OF THE INVENTION

The present invention provides an oil composition containing an oil and 25-hydroxy Vitamin $D_3$, wherein the 25-hydroxy Vitamin $D_3$ is dissolved in the oil in an amount between about 5% and 50% by weight based on the total weight of the oil composition. These oil compositions may be advantageously incorporated into many other compositions, especially emulsions, microencapsulated oils, and feed premixes.

The oil employed in the present invention may be any edible oil or fat, preferably having a high content of lauric acid, e.g., babassu oil, coconut oil, cohune oil, murumyru tallow, palm kernel oil, tucum oil. The oil may be natural, synthetic, semisynthetic, or mixtures thereof. Natural oils may be derived from any source, e.g., animal, plant, fungal, marine. Synthetic and semisynthetic oils may be produced by any convenient means.

Preferred oils are coconut oil, babassu oil, cohune oil and palm kernel oil.

25-hydroxy Vitamin $D_3$ may be obtained from any source. For example, the production of 25-hydroxy Vitamin $D_3$ is described in U.S. Pat. No. 3,565,924, and the isolation of 25-hydroxy Vitamin $D_3$ is described in U.S. Pat. No. 4,310,467.

The oil composition may be prepared by any convenient means. Generally, crystals of 25-hydroxy Vitamin $D_3$ are dissolved in the oil by heating with agitation. Preferably, the oil is first placed in an appropriate vessel and heated to the desired temperature. Thereafter, 25-hydroxy Vitamin $D_3$ is added to the oil, in an appropriate amount, while maintaining the temperature of the oil or increasing it over time. The oil composition is then agitated for a time sufficient to dissolve the crystals of the 25-hydroxy Vitamin $D_3$. Prior to addition to the oil, the 25-hydroxy Vitamin $D_3$ crystals may be reduced in size by any convenient means, including, milling and/or sieving, to enhance dissolving. Agitation may be accomplished by any convenient means, including stirring, vessel rotation, mixing, homogenization, recirculation, and ultrasonication.

Conveniently, the oil is heated to 80-85° C., the 25-hydroxy Vitamin $D_3$ is introduced into the vessel, and the temperature is maintained over two hours while stirring the oil composition.

Generally, 25-hydroxy Vitamin $D_3$ is dissolved in the oil in an amount between about 5% and 50% by weight, based on the total weight of the oil composition. Preferably, the 25-hydroxy Vitamin $D_3$ is dissolved in the oil in an amount between about 10% and 40% by weight based on the total weight of the oil composition; more preferably, in an amount between about 12.5% and 28%; and even more preferably, in an amount between about 15% and 25%

The oil composition may optionally contain any other suitable material including, but not limited to, antioxidants, preservatives, dissolution agents, surfactants, pH adjusting agents or buffers, humectants, and mixtures thereof.

Suitable antioxidants include mixed tocopherols, tocopherols from natural or synthetic sources, ethoxyquin (EMQ) (6-ethoxy-1,2-dihydro-2,2,4-trimethyl-quinoline), butylated hydroxy toluene (BHT), butylated hydroxy anisole (BHA), natural antioxidants like rosemary extract, propyl galate, and mixtures thereof. Preferably, the antioxidant is EMQ.

Suitable preservatives include methyl paraben, propyl paraben, potassium sorbate, sodium benzoate, benzoic acid, and mixtures thereof. Suitable dissolution agents include inorganic or organic solvents, including alcohols, chlorinated hydrocarbons, and mixtures thereof.

Surfactants may be anionic, cationic or nonionic. Suitable surfactants include ascorbyl palmitate, polysorbates, polyethylene glycols, and mixtures thereof. Suitable pH adjusting agents or buffers include citric acid-sodium citrate, phosphoric acid-sodium phosphate, acetic acid-sodium acetate, and mixtures thereof. Suitable humectants include glycerol, sorbitol, polyethylene glycol, propylene glycol, and mixtures thereof.

As appears, the enhanced stability of the various compositions of the present invention is attributable to a physical separation of the labile 25-hydroxy Vitamin $D_3$ component on the one hand, and minerals, transition metals, and/or peroxides often added to animal feed premixes and animal feeds, on the other hand. This enhanced stability is of practical advantage, as shown in the comparative data in the Examples below. Preferably, therefore, the oil compositions of the invention do not contain any minerals, transition metals, or peroxides.

Once formed, the oil composition of the invention may be incorporated in various other useful compositions, some of which are discussed below. For example, emulsions may be formed, which may be converted into various encapsulated oils having superior stability properties.

A variety of emulsions may be prepared by combining the oil compositions described above with an aqueous composition. The emulsion may be of any type. Suitable emulsions include oil-in-water emulsions, water-in-oil emulsions, anhydrous emulsions, solid emulsions, and microemulsions. The emulsions may be prepared by any convenient method.

The emulsions contain an aqueous composition and an oil composition, wherein the oil composition comprises 25-hydroxy Vitamin $D_3$ dissolved in an oil in an amount of between about 5% and about 50% by weight based on the total weight of the oil composition. As used herein, the terms "aqueous composition" and "aqueous phase" are used interchangeably.

Generally, the emulsion contains from about 20% to about 95% of an aqueous composition, and from about 5% to about 80% of an oil composition. Preferably, however, the emulsion contains from about 85% to about 95% of an aqueous composition, and from about 5% to about 15% of an oil composition.

Conveniently, the oil composition may be dispersed as droplets in the aqueous composition. For example, the droplets may have a mean diameter of less than about 500 nm in the aqueous composition. Conveniently, the droplets have a mean diameter of between about 100 nm and about 200 nm.

In a particularly advantageous embodiment, the emulsion contains an encapsulating agent, which facilitates microencapsulating the oil composition upon further processing of the emulsion, e.g., by spray drying. As used herein, the terms "encapsulating agent" and "encapsulation agent" are used interchangeably.

The encapsulating agent may be any edible substance capable of encapsulating the oil composition. Preferably, the encapsulating agent is capable of eliminating contact between the 25-hydroxy Vitamin $D_3$ and the environment when the oil composition is encapsulated by the encapsulating agent. Preferably, the encapsulation agent is predominantly a colloidal material. Such materials include starches, proteins from animal sources (including gelatins), proteins from plant sources, casein, pectin, alginate, agar, maltodextrins, lignin sulfonates, cellulose derivatives, sugars, saccharides, sorbitols, gums, and mixtures thereof.

Suitable starches include: plant starches (e.g., CAPSUL® (National Starch & Chemical Corp., New York, N.Y.), HI-CAP® (National Starch & Chemical Corp., New York, N.Y.)), other modified food starches, and mixtures thereof. Preferably, the starch is CAPSUL®.

Suitable proteins from animal sources include: gelatins (e.g., bovine gelatins, porcine gelatins (Type A or B) with different Bloom numbers, fish gelatins), skim milk protein, caseinate, and mixtures thereof. Preferably, the protein from an animal source is a gelatin. Suitable proteins from plant sources include: potato protein (e.g., ALBUREX® (Roquette Preres Societe Anonyme, Lestrem, France)), pea protein, soy protein, and mixtures thereof. Preferably, the protein from a plant source is ALBUREX® potato protein.

Suitable maltodextrins with a different dextrose equivalent include: maltodextrin 5, maltodextrin 10, maltodextrin 15, maltodextrin 20, maltodextrin 25, and mixtures thereof. Preferably, the maltodextrin is maltodextrin 15.

Suitable cellulose derivatives include: ethyl cellulose, methylethyl cellulose, hydroxypropyl cellulose, hydroxypropylmethyl cellulose, carboxymethylcellulose, and mixture thereof. Suitable saccharides include lactose, sucrose, or mixtures thereof. Preferably, the saccharide is sucrose. Suitable gums include: acacia, locust bean, carragean, and mixtures thereof. Preferably, the gum is gum acacia.

When the emulsion of the invention contains an encapsulating agent, the encapsulating agent may be dispersed in water by any suitable means to form an aqueous phase. The aqueous phase may be a solution or a mixture depending on the properties of the components selected. The selected components may be dispersed by any suitable means including: homogenizing, mixing, emulsifying, recirculating, static mixing, ultrasonication, stirring, heating, and combinations thereof. The viscosity of the resulting aqueous phase may then be adjusted, as desired, by the addition of water.

The aqueous composition of the emulsion may optionally contain any other suitable material including but not limited to, those discussed above in reference to the oil composition. Preferably, the aqueous composition may include, an encapsulating agent, a film-forming agent, a plasticizer, a preservative, an antioxidant, and mixtures thereof.

Suitable antioxidants include sodium ascorbate, ascorbic acid, citric acid, and mixtures thereof. Suitable preservatives include methyl paraben, propyl paraben, sorbic acid, potassium sorbate, sodium benzoate, and mixtures thereof.

Preferably, the aqueous phase contains a modified food starch, such as octenyl succinyl starch (CAPSUL®), maltodextrin, and sodium ascorbate. The selected components may be dissolved in water by any suitable means, preferably stirring. The final viscosity of the resulting aqueous phase may then be adjusted to the desired viscosity, preferably about 250 to about 450 cp, more preferably about 300 to about 400 cp, even more preferably about 385 cp.

Another preferred aqueous phase contains potato protein (ALBUREX®), maltodextrin 20, and sodium ascorbate. The selected components are dispersed into the water, preferably by homogenization. The mixture is preferably homogenized until it is uniform and lump-free. Preferably, the homogenization is carried out at a temperature between about 50° C. and about 75° C.

Preferably, the emulsion compositions of the invention should not contain any mineral, transition metal, or peroxide.

The emulsion may be formed by emulsifying the oil composition and the aqueous phase by any means, including homogenization, rotor-stator shear, high pressure shear and cavitation, high speed "cowles" or shear agitation, and combinations thereof. The volume and viscosity of the emulsion may preferably be adjusted by the addition of water after emulsification.

Conveniently, the oil composition and aqueous composition are emulsified by homogenization.

As noted above, the emulsion may be incorporated or employed in producing other useful compositions, especially microencapsulated oils, e.g., spray dried powders.

Generally, the microencapsulated oils comprise an oil composition and an encapsulation agent encapsulating the oil composition, wherein the oil composition contains 25-hydroxy Vitamin $D_3$ dissolved in the oil in an amount between about 5% and about 50% by weight based on the total weight of the oil composition.

The microencapsulated oil may be produced by any convenient means. Conveniently, the oil composition is encapsulated by drying an emulsion described above by any suitable means, including spray drying, freeze drying, fluid bed drying, tray drying, adsorbtion, and combinations thereof. Preferably, the microencapsulated oil is produced by spray drying an emulsion having an aqueous phase as defined above containing an encapsulation agent. The spray drying parameters are dictated by the physical characteristics desired in the final microencapsulated oil. Such physical parameters include particle size, powder shape and flow, and water content.

Low concentrations of oil in the microencapsulated oil relative to the 25-hydroxy Vitamin $D_3$ leads to enhanced protection of the 25-hydroxy Vitamin $D_3$ and high recovery of the 25-hydroxy Vitamin $D_3$ during the encapsulation process. Conveniently, the oil is in an amount less than about 30% by weight based on the total weight of the microencapsulated oil; more conveniently, less than about 20%, more preferably, less than about 10%; and even more preferably, less than about 5%.

The microencapsulated oil should have good flowability and the 25-hydroxy Vitamin $D_3$ should be distributed homogeneously throughout the composition. Conveniently, the microencapsulated oil is a powder.

Any other suitable additive may be added to the microencapsulated oil. One such additive may be a flow agent such as silicon dioxide, to increase the flowability of the microencapsulated oil.

The microencapsulated oil may be incorporated into or employed in producing various other useful compositions, including feed premix compositions.

For example, the invention provides a feed premix composition containing a microencapsulated oil of the invention and at least one nutritional additive.

As used herein the term "nutritional additive" means any substance added to animal feeds and animal feed premixes to add nutritional value to the product, to adjust the nutritional value of the product, or to aid in the addition of nutritional value to the product. Suitable nutritional additives include: vitamins, pro vitamins, minerals, active phytase, amino acids, carotenoids, starches, fish meal, choline, medicinal additives, carriers, and combinations thereof.

Suitable vitamins include all vitamins and derivatives thereof (Vitamin A, Vitamin E, Vitamin $B_{12}$, Vitamin $B_3$, Niacin, d-pantothenic acid, Folic Acid, Vitamin $B_6$, Vitamin $B_1$, Vitamin $D_3$, Vitamin C, Vitamin $B_2$, and combinations thereof.) Any pro vitamin or mixture of pro vitamins may be employed, such as beta-carotene. Suitable minerals and their salts include manganese, zinc, iron sulfate (monohydrate), copper oxide, cobalt sulfate Iodine, selenium, and combinations thereof.

Any suitable amino acid may be employed. Suitable carotenoids include: CAROPHYLL® Red (Roche Vitamins Inc., Parsippany, N.J.), beta carotene, astaxanthin, and combinations thereof. Suitable starches include: corn starch, wheat starch, potato starch, tapioca starch, and combinations thereof.

Suitable medicinal additives include: pharmaceuticals, performance enhancers, antibiotics, antioccidials, and mixtures thereof. Suitable carriers include: limestone, wheat middlings, corn meal, rice hulls, calcium carbonate, and combinations thereof.

Conveniently, the feed premix composition contains Vitamin A, Vitamin E, Vitamin $B_{12}$, Vitamin $B_3$, niacin, d-pantothenic acid, folic acid, Vitamin $B_6$, Vitamin $B_1$, limestone, and rice hulls.

Another preferred feed premix composition contains Vitamin E, Vitamin $B_3$, cartenoids, choline chloride, manganese oxide, zinc oxide, iron sulphate, copper oxide, cobalt sulphate, and wheat middlings. Still another preferred feed premix composition of the invention contains a phytase enzyme.

The feed premix composition may be produced by any convenient means known in the art by combining the microencapsulated oil with any selected nutritional additives; including by mixing, adhesion, dispersion of the microencapsulated ingredient in an appropriate solvent and spraying onto the nutritional additive, and combinations thereof. Conveniently, the feed premix composition is produced by mixing the microencapsulated oil with any selected nutritional additives.

The feed premix compositions may be added to a variety of animal food products. For example, they may be added to poultry (e.g., fryers, broilers, layers, turkeys) feed, swine, canine, and feline feed.

Generally, the premix is combined with the animal food product in an amount to provide 50 ppb to 200 ppb (parts-per-billion) 25-hydroxy Vitamin $D_3$ based on the finished feed.

The following examples are provided to further illustrate the compositions and methods of the present invention. These examples are illustrative only and are not intended to limit the scope of the invention in any way.

EXAMPLES

Example 1

Oil Compositions

Oil compositions of the present invention are prepared by dissolving 25-hydroxy Vitamin $D_3$ in an oil with heating and/or agitation, in the following proportions.

TABLE 1

Oil compositions.

| Amount of 25-hydroxy Vitamin $D_3$ | Oil | Amount of Oil (g) | % wt of 25-hydroxy Vitamin $D_3$ |
|---|---|---|---|
| 5 | Coconut | 95 | 5 |
| 5 | Palm Kernel | 95 | 5 |
| 10 | Coconut | 90 | 10 |
| 10 | Palm Kernel | 90 | 10 |
| 15 | Coconut | 85 | 15 |
| 15 | Palm Kernel | 85 | 15 |
| 20 | Coconut | 80 | 20 |
| 20 | Palm Kernel | 80 | 20 |
| 25 | Coconut | 75 | 25 |
| 25 | Palm Kernel | 75 | 25 |
| 30 | Coconut | 70 | 30 |
| 30 | Palm Kernel | 70 | 30 |
| 35 | Coconut | 65 | 35 |
| 35 | Palm Kernel | 65 | 35 |
| 40 | Coconut | 60 | 40 |
| 40 | Palm Kernel | 60 | 40 |
| 45 | Coconut | 55 | 45 |
| 45 | Palm Kernel | 55 | 45 |
| 50 | Coconut | 50 | 50 |
| 50 | Palm Kernel | 50 | 50 |

Example 2

Oil Compositions

The oil compositions of the present invention are prepared by dissolving 25-hydroxy Vitamin $D_3$ and an antioxidant in an oil with heating and/or agitation, in the following proportions.

TABLE 2

Oil compositions containing an antioxidant.

| Amount of 25-hydroxy Vitamin $D_3$ (g) | Oil | Amount of Oil (g) | Anti-oxidant | Amount of Anti-oxidant (g) | % wt of 25-hydroxy Vitamin $D_3$ |
|---|---|---|---|---|---|
| 5 | Coconut | 85 | EMQ | 10 | 5 |
| 5 | Coconut | 75 | BHT | 20 | 5 |
| 5 | Palm Kernel | 85 | EMQ | 10 | 5 |
| 5 | Palm Kernel | 75 | BHT | 20 | 5 |
| 15 | Coconut | 75 | EMQ | 10 | 15 |
| 15 | Coconut | 65 | BHT | 20 | 15 |
| 15 | Palm Kernel | 75 | EMQ | 10 | 15 |
| 15 | Palm Kernel | 65 | BHT | 20 | 15 |
| 30 | Coconut | 60 | EMQ | 10 | 30 |
| 30 | Coconut | 50 | BHT | 20 | 30 |
| 30 | Palm Kernel | 60 | EMQ | 10 | 30 |
| 30 | Palm Kernel | 50 | BHT | 20 | 30 |
| 40 | Coconut | 50 | EMQ | 10 | 40 |
| 40 | Coconut | 40 | BHT | 20 | 40 |
| 40 | Palm Kernel | 50 | EMQ | 10 | 40 |
| 40 | Palm Kernel | 40 | BHT | 20 | 40 |
| 50 | Coconut | 40 | EMQ | 10 | 50 |
| 50 | Coconut | 30 | BHT | 20 | 50 |
| 50 | Palm Kernel | 40 | EMQ | 10 | 50 |
| 50 | Palm Kernel | 30 | BHT | 20 | 50 |

Example 3

Emulsion

An emulsion according to the present invention was prepared by dispersing an oil composition according to the present invention (e.g., those of Examples 1 and 2) in an aqueous composition.

The oil composition contained: 7.2 kg of 25-hydroxy Vitamin $D_3$; 27.6 kg coconut oil; and 19.88 kg EMQ. The oil composition was produced by mixing the coconut oil, EMQ, and 25-hydroxy Vitamin $D_3$ and heating to approximately 85° C. Stirring was continued for 90 minutes at a constant temperature. At this time, all of the crystals of 25-hydroxy Vitamin $D_3$ had gone into solution, as determined by viewing the solution under a microscope.

The aqueous composition contained: 376.35 kg of CAP-SUL®; 78.09 kg of maltodextrin 15; 12.81 kg of sodium ascorbate; and 437.64 kg of water. To prepare the aqueous phase the ingredients were combined. With mixing and heating the dry ingredients readily dissolved in the water. The viscosity of this solution was about 385 cps.

The oil composition was added to the aqueous composition and homogenized in a homogenizer for 30 minutes. During homogenization an emulsion was formed wherein the droplets of the oil composition have a diameter of approximately 150 nm Example 4

Microencapsulated Oil Composition

A microencapsulated oil composition of the present invention was prepared by spray drying the emulsion of Example 3 using the following parameters:

| | |
|---|---|
| Inlet Temperature | 135° C. |
| Outlet Temperature | 102° C. |
| Microclone Inlet | 4.1 |
| Fan Inlet | 14.6 |
| Silica Feeder | Set to provide about 1% Silica in dry product |
| Atomizer RPM | 17000 part A |
| | 15000 part B |
| Pump Speed | 17 part A |
| | 21 part B |
| Product Moisture | 1.9 to 2.25% |

The microencapsulated oil was a tan powder having the following characteristics:

| | |
|---|---|
| Loose Bulk Density | ~0.42 g/ml |
| Tapped Bulk Density | ~0.5 g/ml |
| Dust | ~169 mg/25 g |
| Angle of Repose | ~49° |
| Agway Flow | None |
| Loss on Drying | ~2.6 % |

In addition, the microencapsulated oil composition showed a high degree of homogeneity as measured by UV absorptivity of the powder.

Example 5

Stability

Two batches of a microencapsulated oil composition of the present invention (Invention 001 and Invention 002) were produced as set forth below. The stability of these batches was compared to a prior art commercial product in the form of a wax beadlet. The two batches and the commercial product were all stored at either 11° C. or 25° C. for up to 4 months.

The two batches tested contained approximately 1.25% wt of 25 hydroxy Vitamin $D_3$ prepared according to Examples 3 and 4.

The following data demonstrate that the microencapsulated oils of the present invention exhibited greatly increased stability over the commercial product. Additionally, the microencapsulated oils of the present invention showed a slowdown in the degradation kinetic, indicating that the rate of degradation of 25-hydroxy Vitamin $D_3$ greatly decreases after an initial period of storage.

Storage Conditions:

The batches according to the present invention and the commercial product are stored under conventional conditions at various temperatures (see below) for period of up to 4 months.

Results:

Batch 001 displays higher initial values for 25-hydroxy Vitamin $D_3$ content than Batch 002.

Storage at 11° C.

Figure 1:
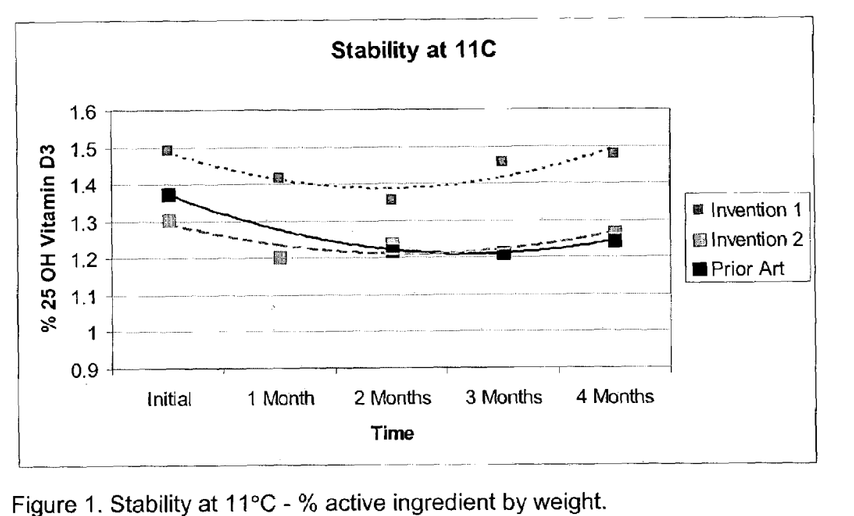
FIG. 1 shows the % Vitamin $D_3$ retention of 25-hydroxy Vitamin $D_3$ (% active ingredient by weight of total composition) in microencapsulated oils according to the present invention as compared to a prior art formulation at various storage times at 11° C.
Figure 2:
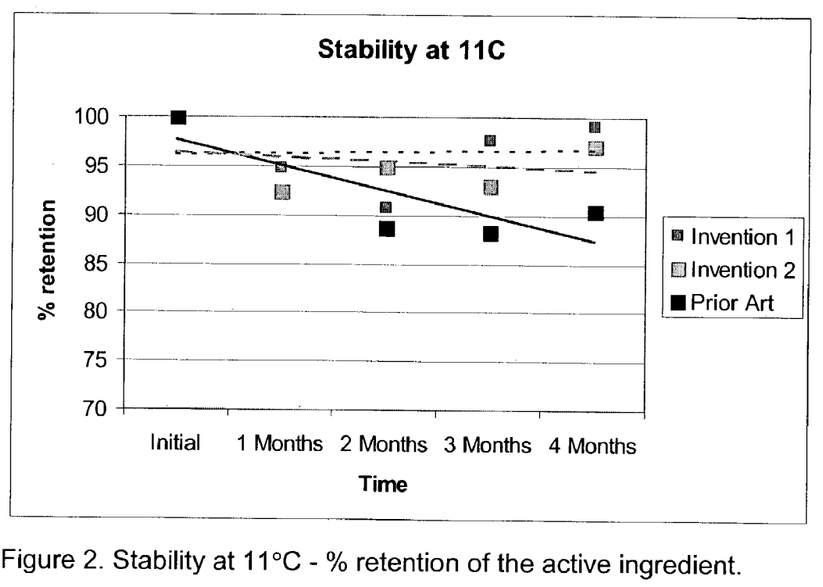
FIG. 2 shows the percent retention of 25-hydroxy Vitamin $D_3$ in microencapsulated oils according to the present invention as compared to a prior art formulation at various storage times at 11° C.

As FIG. 1 shows, the compositions of the present invention displayed improved stability compared to the commercial product, at all time points, when stored at 11° C. FIG. 2 shows a plateau in the % 25-hydroxy Vitamin $D_3$ retention and demonstrates a slowdown of the degradation kinetic in the compositions of the present invention.

Storage at 25° C.

Figure 3:
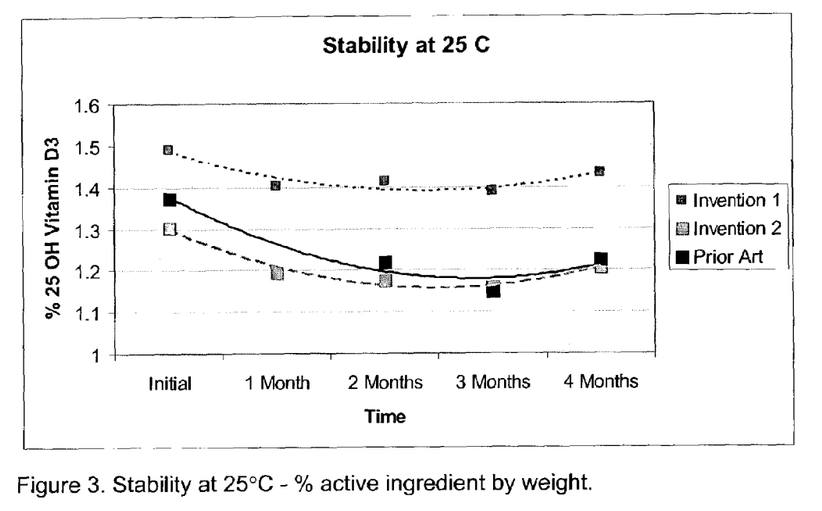
FIG. 3 shows the % Vitamin $D_3$ retention of 25-hydroxy Vitamin $D_3$ (% active ingredient by weight of total composition) in microencapsulated oils according to the present invention as compared to a prior art formulation at various storage times at 25° C.
Figure 4:
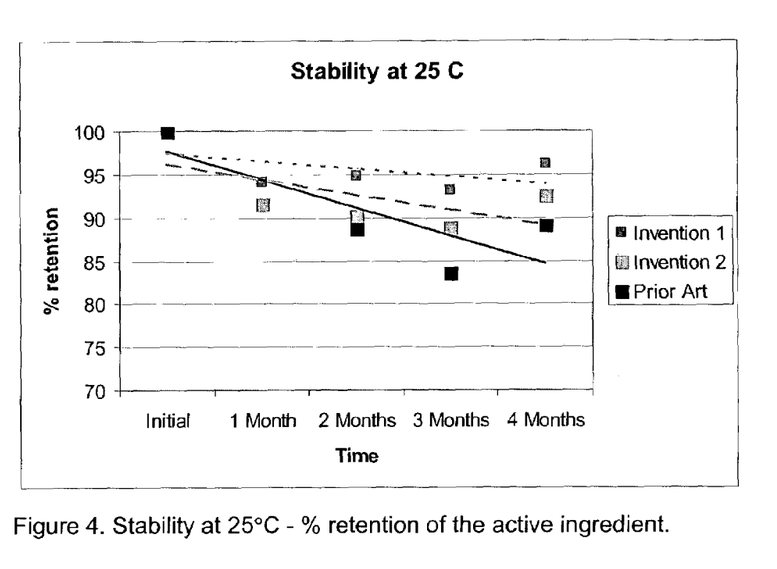
FIG. 4 shows the percent retention of 25-hydroxy Vitamin $D_3$ in microencapsulated oils according to the present invention as compared to a prior art formulation at various storage times at 25° C.

As FIG. 3 shows, the compositions of the present invention displayed improved stability compared to the commercial product, at all time points, when stored at 25° C. FIG. 4 shows a plateau in the 25-hydroxy Vitamin $D_3$% retention at 25° C., and demonstrates a slowdown of the degradation kinetic in the compositions of the present invention.

Storage at 37° C.

At this temperature, the prior art beadlets began to degrade and form a solid block that was no longer a powder. For this reason, the prior art beadlet could not be dissolved in the solvent as usual, and no reliable retention data could be obtained. The compositions of the present invention suffered from no such degradation, and retained good flowability and bulk density at this elevated storage temperature at all time points.

Figure 5:
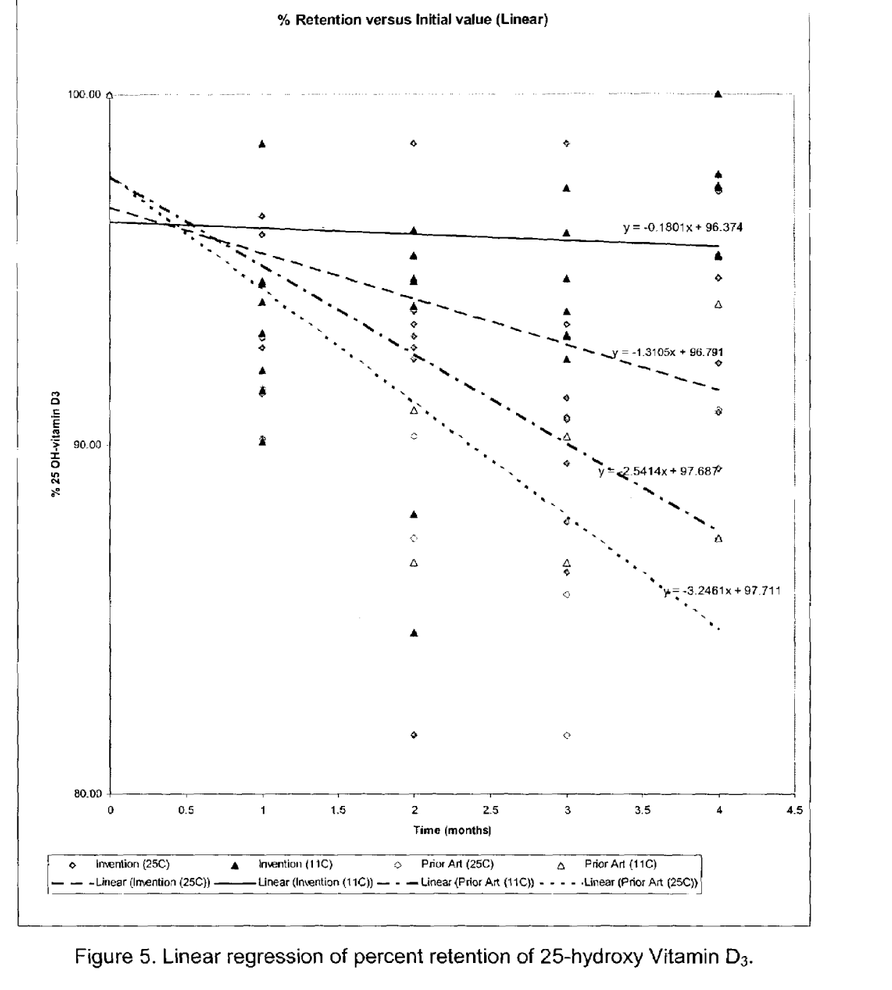
FIG. 5 shows the linear regression of 25-hydroxy Vitamin $D_3$ retention data for microencapsulated oils according to the present invention as compared to a prior art formulation at various storage times at various temperatures.

FIG. 5 shows the linear regression of the retention data for the 25-hydroxy Vitamin $D_3$, and the commercial product at various temperatures. The regression demonstrates that the compositions of the present invention have a greatly improved stability over the commercial product at both temperatures and at all storage times. In addition, the slope of the regression curves clearly shows that the rate of degradation for the 25-hydroxy Vitamin $D_3$ in the microencapsulated oil compositions of the present invention is much less than that of the prior art beadlet at all storage times and temperatures. Accordingly, even after a short storage time the compositions of the present invention will retain significantly more 25-hydroxy Vitamin $D_3$ as compared to the prior art beadlet.

Example 6

Premix Composition

A basic premix for use in animal feed was prepared having the following components in the following proportions by percent weight based on the total weight of the premix.

TABLE 3

Premix composition

| COMPONENT | % WEIGHT IN PREMIX |
|---|---|
| 25-hydroxy Vitamin $D_3$, 1.25% | 0.64 |
| Vitamin A | 6.40 |
| Vitamin E | 16.00 |
| Vitamin $B_{12}$ | 6.40 |
| Vitamin $B_3$ | 2.00 |
| Niacin | 8.00 |
| Calcium Pantothenate | 4.00 |
| Vitamin $K_3$ | 0.94 |
| Folic Acid | 0.90 |
| Vitamin $B_6$ | 0.96 |
| Vitamin $B_1$ | 0.62 |
| Limestone | 29.00 |
| Rice Hulls | 24.14 |

Example 7

Premix Stability

Three premixes for use in animal feed were prepared having the following components in the following proportions by percent weight based on the total weight of the premix.

TABLE 4

Composition of premixes.

| COMPONENT | COMPLETE | VITAMIN | BASIC |
|---|---|---|---|
| 25-hydroxy Vitamin $D_3$, 1.25% | 0.50 | 1.00 | 1.57 |
| Vitamin $D_3$ | | 0.64 | |
| Vitamin A | | 6.40 | |
| Vitamin E | 0.40 | 16.00 | |
| Vitamin $B_{12}$ | | 6.40 | |
| Vitamin $B_3$ | 0.05 | 2.00 | |
| Niacin | | 8.00 | |
| Calcium Pantothenate | | 4.00 | |
| Vitamin $K_3$ | | 0.94 | |
| Folic Acid | | 0.90 | |
| Vitamin $B_6$ | | 0.96 | |
| Vitamin $B_1$ | | 0.62 | |
| Carotenoids | 0.20 | | |
| Choline Chloride, 50% | 1.50 | | |
| Manganese Oxide | 3.00 | | |
| Zinc Oxide | 0.60 | | |

TABLE 4-continued

Composition of premixes.

| COMPONENT | COMPLETE | VITAMIN | BASIC |
|---|---|---|---|
| Iron Sulphate (monohydrous) | 1.00 | | |
| Copper Oxide | 0.10 | | |
| Cobalt Sulphate | 0.01 | | |
| Oil | | | 1.00 |
| Limestone | | 28.00 | 19.93 |
| Rice Hulls | | 24.14 | 77.50 |
| Wheat Middlings | 78.99 | | |

Each of these premix compositions was prepared using a microencapsulated oil of the present invention or a prior art beadlet containing 25-hydroxy Vitamin $D_3$. In addition, a control formulation was prepared, in which Vitamin $D_3$ was substituted for the 25-hydroxy Vitamin $D_3$. Each of the premixes was stored at 25° C. and 35° C., for a length of time up to 3 months. The percent retention of the 25-hydroxy Vitamin $D_3$ was determined at each time and temperature.

Figure 6:
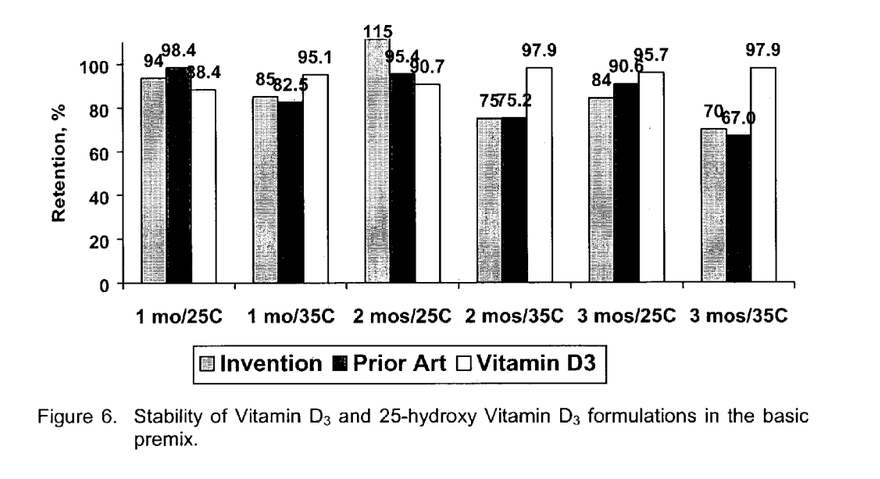
FIG. 6 shows the percent retention in of Vitamin $D_3$ and 25-hydroxy Vitamin $D_3$ in prior art and 25-hydroxy Vitamin $D_3$ Basic Premixes of the present invention.
Figure 7:
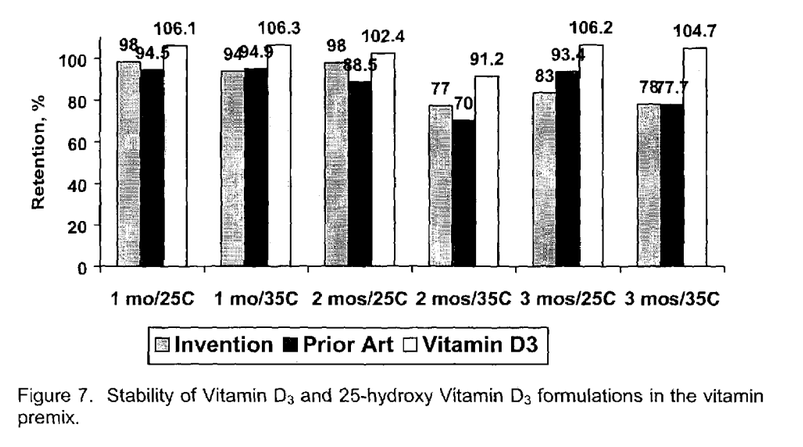
FIG. 7 shows the percent retention of Vitamin $D_3$ and 25-hydroxy Vitamin $D_3$ in prior art and 25-hydroxy Vitamin $D_3$ Vitamin Premixes of the present invention.
Figure 8:
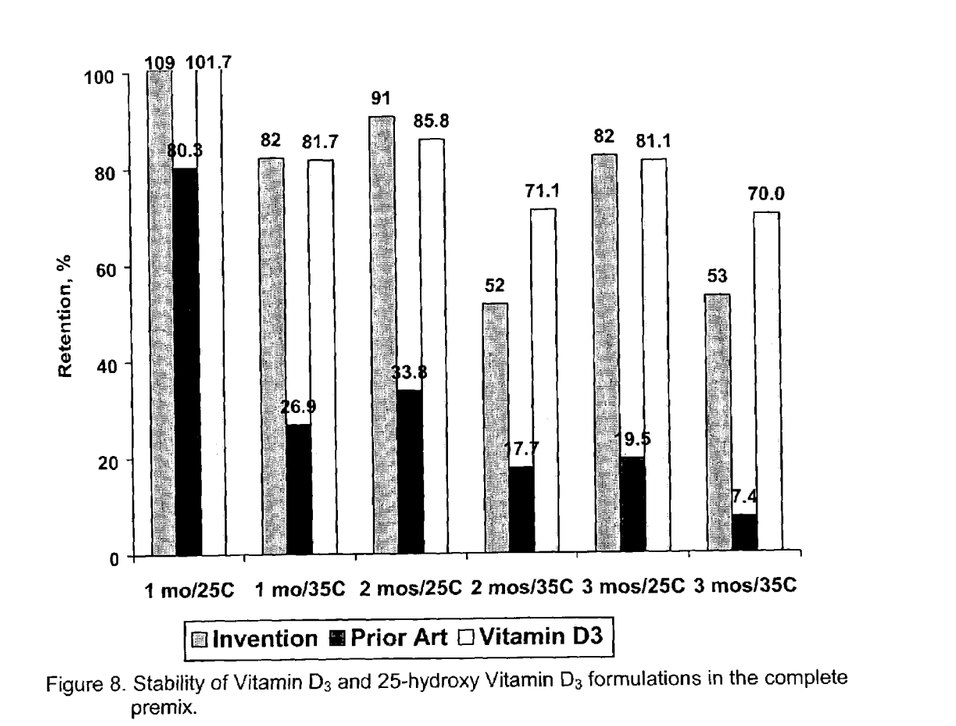
FIG. 8 shows the percent retention of Vitamin $D_3$ and 25-hydroxy Vitamin $D_3$ in prior art and 25-hydroxy Vitamin $D_3$ Complete Premixes of the present invention.

FIG. 6 shows the % retention of the 25-hydroxy Vitamin $D_3$ in the Basic Premix at each time and temperature. FIG. 7 shows the % retention of the 25-hydroxy Vitamin $D_3$ in the Vitamin Premix at each time and temperature. FIG. 8 shows the % retention of the 25-hydroxy Vitamin $D_3$ in the Complete Premix at each time and temperature.

As the results show, in the Basic and Vitamin Premixes the stability of 25-hydroxy Vitamin $D_3$ was less than that of Vitamin $D_3$. However, the stability the 25-hydroxy Vitamin $D_3$ was nearly identical for the prior art formulation as compared to the formulations in accordance with the present invention. (See FIGS. 6 and 7).

The results are dramatically different when the Complete Premix is considered, however. As shown in FIG. 8, the stability of the 25-hydroxy Vitamin $D_3$ in the prior art formulation dropped significantly as compared to the inventive formulations. As discussed above, this decrease in stability may be attributed to the oxidation of the Vitamin $D_3$ or 25-hydroxy Vitamin $D_3$ by minerals, transition metals, or peroxides found in the premix. For example, at three months storage, the prior art formulation retained less than 20% of the 25-hydroxy Vitamin $D_3$, whereas the formulation in accordance with the present invention retained better than 50% of the 25-hydroxy Vitamin $D_3$ (over 80% at a storage temperature of 25° C.).

The formulation of the present invention thus increased 25-hydroxy Vitamin $D_3$ retention over a wide range of temperatures and times of storage, even in premixes containing components which promote degradation of 25-hydroxy Vitamin $D_3$.

Example 8

Feeds

An animal feed composition was produced by combining the feed premix compositions of the present invention with an animal feed. A poultry feed was produced by mixing the premix of Example 6 with a base poultry feed having the following ingredients:

TABLE 5

Composition poultry base feed ingredients.

| INGREDIENT | AMOUNT (% WT) |
|---|---|
| Corn | 50.55 |
| Soybean Meal | 40.05 |
| Soybean Oil | 5.00 |
| Dicalcium Phosphate | 1.90 |
| Limestone | 1.40 |
| Salt | 0.40 |
| $D_3$-free Vitamin Mix | 0.20 |
| Mineral Mix | 0.15 |
| DL-Met | 0.20 |
| Choline 60 | 0.10 |
| Bacitracin | 0.025 |
| α-Tocopherol | 0.002 |
| Ethoxyquin | 0.0125 |

The premix and base feed were mixed until substantial homogeneity was produced.

The invention being thus described, it will be obvious that the same may be varied in many ways. Such variations are not to be regarded as a departure from the spirit and scope of the invention and all such modifications are intended to be included within the scope of the following claims.

We claim:

1. A stabilized encapsulated oil composition encapsulated by an encapsulating agent, wherein the oil composition comprises:

25-hydroxy Vitamin D3 dissolved in a plant oil in an amount between about 10% and 28% by weight based on the total weight of the oil composition, the amount of the plant oil less than about 30% by weight based on the total weight of the oil composition, an antioxidant selected from the group consisting of: mixed tocopherols, tocopherols from natural or synthetic sources, ethoxyquin, butylated hydroxy toluene, butylated hydroxy anisole, and natural antioxidants, the encapsulating agent is selected from the group consisting of: gelatin, a modified food starch, plant protein, a maltodextrin, a cellulose derivative, a saccharide, a gum, and mixtures thereof;

and the encapsulated oil composition is a powder.

2. An encapsulated oil composition according to claim 1 wherein the plant oil is selected from the group consisting of: babassu oil, coconut oil, cohune oil, murumyru tallow, palm kernel oil, tucum oil, and mixtures thereof.

3. An encapsulated oil composition according to claim 1, wherein the oil is an amount less than about 20% by weight based on the total weight of the oil composition.

4. An encapsulated oil composition according to claim 1, wherein the oil is an amount less than about boo by weight based on the total weight of the oil composition.

5. An encapsulated oil composition according to claim 1 wherein the oil composition comprises: a plant oil and ethoxyquin, the encapsulating agent comprises a modified food starch, and a maltodextrin, and wherein the encapsulated oil composition further comprises silicon dioxide.

6. A stabilized feed premix composition comprising:

an encapsulated oil composition encapsulated by an encapsulating agent, wherein the oil composition comprises:

25-hydroxy Vitamin D3 dissolved in a plant oil in an amount between about 10% and 28% by weight based on the total weight of the oil composition, the amount of the plant oil less than about 30% by weight based on the total weight of the oil composition, an antioxidant selected from the group consisting of: mixed tocopherols, tocopherols from natural or synthetic sources, ethoxyquin, butylated hydroxy toluene, butylated hydroxy anisole, and natural antioxidants, the encapsulating agent is selected from the group consisting of: gelatin, a modified food starch, plant protein, a maltodextrin, a cellulose derivative, a saccharide, a gum, and mixtures thereof;

and wherein the oil composition is in the form of a powder;

and at least one nutritional additive.

7. A feed premix composition according to claim 6 wherein the nutritional additive is selected from the group consisting of: vitamin, pro vitamins, minerals, active phytase, amino acids, carotenoids, starches, fish meal, choline, medicinal additives, carriers, and combinations thereof.

8. A feed premix composition according to claim 7 wherein the nutritional additive comprises a vitamin.

9. A feed premix composition according to claim 8 wherein the vitamin is selected from the group consisting of: Vitamin A, Vitamin L, Vitamin B12, Vitamin B3, Niacin, d-pantothenic acid, Folic Acid, Vitamin B6, Vitamin B1, Vitamin D3, Vitamin C, Vitamin B2, and combinations thereof.

10. A feed premix according to claim 9 wherein the vitamin comprises Vitamin D3.

11. A feed premix according to claim 6 which is suitable for poultry, swine, canine, or feline feed.

12. A feed premix according to claim 11 which is suitable for poultry feed.

13. A feed premix according to claim 11 which is suitable for swine feed.

14. A feed premix according to claim 11 which is suitable for canine feed.

15. A feed premix according to claim 10 which is suitable for poultry, swine, canine, or feline feed.

16. A feed premix according to claim 15 which is suitable for poultry feed.

17. A feed premix according to claim 15 which is suitable for swine feed.

18. A feed premix according to claim 15 which is suitable for canine feed.

19. A stabilized animal feed product comprising a feed premix composition according to claim 6 and an animal feed.

20. An animal feed product according to claim 19 wherein the animal feed is selected from the group consisting of poultry, swine, canine, and feline feeds.

21. An animal feed product according to claim 20 which is poultry feed.

22. An animal feed product according to claim 20 which is swine feed.

23. An animal feed product according to claim 20 which is canine feed.

24. A stabilized animal feed product comprising a feed premix composition according to claim 10 and an animal feed.

25. An animal feed product according to claim 24 which is poultry feed.

26. An animal feed product according to claim 24 which is swine feed.

27. An animal feed product according to claim 24 which is canine feed.

28. A stabilized animal feed premix comprising a stabilized encapsulated oil composition according to claim 6,
wherein the Vitamin D3 retains at least 50% of the 25-hydroxy vitamin D3 activity after three months of storage at 25 degrees C.

29. A stable 25-hydroxy vitamin D3 beadlet comprising an encapsulated oil composition according to claim 6, wherein the beadlet is in powder form after three months of storage at 37 degrees C.

* * * * *